(12) United States Patent
Aschmann et al.

(10) Patent No.: US 8,968,365 B2
(45) Date of Patent: Mar. 3, 2015

(54) INTERSPINOUS SPACER

(75) Inventors: Felix Aschmann, Basel (CH); Martin Oswald, Meilen (CH); Peter Senn, Waldenburg (CH); Hansjuerg Emch, Swarthmore, PA (US); Grant A. Skidmore, Virginia Beach, VA (US); Heinz Michael Mayer, Graefelfing (DE)

(73) Assignee: DePuy Synthes Products, LLC, Raynham, MA (US)

( * ) Notice: Subject to any disclaimer, the term of this patent is extended or adjusted under 35 U.S.C. 154(b) by 290 days.

(21) Appl. No.: 12/677,751

(22) PCT Filed: Sep. 11, 2008

(86) PCT No.: PCT/US2008/075997
§ 371 (c)(1),
(2), (4) Date: Mar. 11, 2010

(87) PCT Pub. No.: WO2009/036156
PCT Pub. Date: Mar. 19, 2009

(65) Prior Publication Data
US 2010/0204732 A1 Aug. 12, 2010

Related U.S. Application Data

(60) Provisional application No. 60/972,572, filed on Sep. 14, 2007.

(51) Int. Cl.
*A61B 17/70* (2006.01)
(52) U.S. Cl.
CPC ......... *A61B 17/7062* (2013.01); *A61B 17/7053* (2013.01)
USPC ........................................... 606/248; 606/249
(58) Field of Classification Search
USPC ................................. 606/246, 248, 249, 263; 623/17.11–17.16
See application file for complete search history.

(56) References Cited

U.S. PATENT DOCUMENTS 3,482,012 A  12/1969  Baklor
3,745,590 A  7/1973  Stubstad
(Continued)

FOREIGN PATENT DOCUMENTS

CH  SU 1484348  6/1989
DE  31 13 142 A1  1/1982
(Continued)

OTHER PUBLICATIONS

PCT International Search Report.
(Continued)

*Primary Examiner* — Mary Hoffman
*Assistant Examiner* — Christina Negrellirodrigue
(74) *Attorney, Agent, or Firm* — Meunier Carlin & Curfman, LLC (57) ABSTRACT

The present invention relates to an interspinous spacer (10, 10', 10", 10''', 10'''', 10''''') for implantation between adjacent spinous process (SP) to treat spinal stenosis. The interspinous spacer preferably includes a W-shaped or S-shaped leaf spring body member (21) for insertion between adjacent spinous processes and one or more wire straps (42) extending from the body to attach the spacer to the adjacent spinous processes. The wire straps are preferably sized and configured to extend from one side of the leaf spring, along one side of a spinous process, over or under the spinous process to the other side wherein the wire strap can be coupled to the leaf spring. Alternatively, the spacer may include one or more hooks (60) for engaging one or both of the adjacent spinous processes. Preferably, the top bone contacting surface (22) has a more accentuated convex shape compared to the bottom surface (24) so that the spacer is better able to sit in the naturally formed concavity present in the bottom surface of a spinous process.

28 Claims, 13 Drawing Sheets

(56) References Cited

U.S. PATENT DOCUMENTS

| | | |
|---|---|---|
| 4,187,390 A | 2/1980 | Gore |
| 4,313,232 A | 2/1982 | Habal et al. |
| 4,531,916 A | 7/1985 | Scantlebury et al. |
| 4,576,608 A | 3/1986 | Homsy |
| 5,011,497 A | 4/1991 | Persson et al. |
| 5,062,851 A | 11/1991 | Branemark |
| 5,092,866 A | 3/1992 | Breard et al. |
| 5,098,779 A | 3/1992 | Kranzler et al. |
| 5,152,782 A | 10/1992 | Kowligi et al. |
| 5,180,381 A | 1/1993 | Aust et al. |
| 5,180,393 A | 1/1993 | Commarmond |
| 5,306,310 A | 4/1994 | Siebels |
| 5,387,213 A | 2/1995 | Breard et al. |
| 5,395,372 A | 3/1995 | Holt et al. |
| 5,415,661 A | 5/1995 | Holmes |
| 5,491,882 A | 2/1996 | Walston et al. |
| 5,496,318 A | 3/1996 | Howland et al. |
| 5,507,823 A | 4/1996 | Walston et al. |
| 5,554,191 A | 9/1996 | Lahille et al. |
| 5,645,599 A * | 7/1997 | Samani ............... 623/17.16 |
| 5,674,296 A | 10/1997 | Bryan et al. |
| 5,676,702 A | 10/1997 | Ratron |
| 5,879,396 A | 3/1999 | Walston et al. |
| 5,928,284 A | 7/1999 | Mehdizadeh |
| 6,206,923 B1 | 3/2001 | Boyd et al. |
| 6,231,609 B1 | 5/2001 | Mehdizadeh |
| 6,440,169 B1 * | 8/2002 | Elberg et al. ............... 623/17.16 |
| 6,475,219 B1 | 11/2002 | Shelokov |
| 6,572,653 B1 | 6/2003 | Simonson |
| 6,641,585 B2 | 11/2003 | Sato et al. |
| 6,743,257 B2 | 6/2004 | Castro |
| 6,761,720 B1 | 7/2004 | Senegas |
| 6,913,621 B2 | 7/2005 | Boyd et al. |
| 6,966,910 B2 | 11/2005 | Ritland |
| 6,986,771 B2 | 1/2006 | Paul et al. |
| 7,052,515 B2 | 5/2006 | Simonson |
| 7,238,204 B2 | 7/2007 | Le Couedic et al. |
| 2002/0143331 A1 | 10/2002 | Zucherman et al. |
| 2003/0083749 A1 | 5/2003 | Kuslich et al. |
| 2004/0249463 A1 | 12/2004 | Bindseil et al. |
| 2005/0085815 A1 | 4/2005 | Harms et al. |
| 2005/0102028 A1 | 5/2005 | Arnin et al. |
| 2005/0124991 A1 | 6/2005 | Jahng |
| 2005/0125063 A1 | 6/2005 | Matge et al. |
| 2005/0203624 A1 | 9/2005 | Serhan et al. |
| 2006/0015181 A1 | 1/2006 | Elberg |
| 2006/0142760 A1 | 6/2006 | McDonnell |
| 2006/0241601 A1 | 10/2006 | Trautwein et al. ............... 606/61 |
| 2007/0191837 A1 | 8/2007 | Trieu ............... 606/61 |
| 2007/0265626 A1 * | 11/2007 | Seme ............... 606/61 |
| 2008/0033552 A1 | 2/2008 | Lee et al. |
| 2008/0281423 A1 | 11/2008 | Sheffer et al. ............... 623/17.11 |
| 2008/0319487 A1 * | 12/2008 | Fielding et al. ............... 606/263 |
| 2010/0204732 A1 | 8/2010 | Aschmann et al. |

FOREIGN PATENT DOCUMENTS

| | | |
|---|---|---|
| EP | 0 322 334 A1 | 6/1989 |
| EP | 0529275 A2 | 3/1993 |
| EP | 1139929 B1 | 3/2004 |
| EP | 1 330 987 A1 | 5/2006 |
| EP | 1 872 731 | 2/2008 |
| FR | 2 681 525 | 3/1993 |
| FR | 2 812 806 | 2/2002 |
| FR | 2843017 A1 | 2/2004 |
| FR | 2 892 616 | 5/2007 |
| JP | 2002095672 A | 4/2002 |
| JP | 2003516173 | 5/2003 |
| JP | 2007505720 | 3/2007 |
| WO | WO 01/62190 | 8/2001 |
| WO | 2004012634 A2 | 12/2004 |
| WO | WO 2005/032432 | 4/2005 |
| WO | 2006110578 | 10/2006 |
| WO | WO 2008/091112 | 7/2008 |
| WO | 2009036156 A1 | 3/2009 |

OTHER PUBLICATIONS

Le U—DAS System ZUR Dynamischen Stabilisierung.
Fixano Interspinous U.
Experiences preliminaires avec le "U" interepineux.
Office Action, dated Oct. 19, 2011, received from the China Patent Office in connection with Chinese Patent Application No. 2008801071641 (English translation).
European Patent Application No. 08799465.3, "Communication pursuant to Article 94(3) EPC," issued Mar. 16, 2012 (5 pages).
PCT International Search Report, Dec. 9, 2008.
Future of Spine Surgery "Beyond Total Disc"—Fixano SA Interspinous U Fixation System, dated 2004.
Fixano Interspinous U, Jan. 25, 2008.
Experiences preliminaires avec le "U" interepineux, Jan. 23, 2008.

* cited by examiner

INTERSPINOUS SPACER

CROSS-REFERENCE TO RELATED APPLICATIONS

This application claims the benefit of U.S. Provisional Application No. 60/972,572, filed on Sep. 14, 2007, entitled "INTERSPINOUS SPACER," the contents of which is incorporated in its entirety by reference herein.

BACKGROUND OF THE INVENTION

A human vertebra has a rearwardly projecting portion known as a spinous process. Bending of the spine can cause the spinous processes of adjacent vertebrae to move with respect to one another (e.g. toward and/or away). This may, in turn, constrict the space in the spinal canal and foramina and, thus, may cause pain. Such constriction, which is known as stenosis, can be treated by inserting a spacer into the space between adjacent spinous processes.

Generally speaking there are two types of spinal stenosis: (1) hard or rigid spinal stenosis or (2) soft or dynamic spinal stenosis. In both cases, spinal stenosis may be caused by excessive growth of tissue due to degeneration, loss of disc height, as well disorders such as spondilolisthesis where the normal relative position and/or orientation of the adjacent vertebrae have been modified.

The most significant difference between the two types of spinal stenosis is that generally speaking dynamic spinal stenosis may be treated with distraction of the vertebra at the affected level while hard stenosis generally requires removal of the tissue that obstructs the spinal canal or foramina at the affected level. In case of tissue removal, the patient generally must accept some loss of stability of the spine. Therefore, it is preferable to increase the stability of the spinal segment by inserting an interspinous spacer in between the adjacent vertebrae to increase the stiffness of the segment and/or to restrict motion of that segment.

SUMMARY OF THE INVENTION

The present invention relates to an interspinous spacer for implantation between adjacent spinous processes to treat spinal stenosis. The interspinous spacer preferably includes a W-shaped or S-shaped leaf spring body member for insertion between adjacent spinous processes and one or more wire straps extending from the body to attach the spacer to the adjacent spinous processes. The wire straps are preferably sized and configured to extend from one side of the leaf spring, along one side of a spinous process, over or under the spinous process to the other side wherein the wire strap can be coupled to the leaf spring. Alternatively, the spacer may include one or more hooks for engaging one or both of the adjacent spinous processes. Preferably, the top bone contacting surface has a more accentuated convex shape compared to the bottom surface so that the spacer is better able to sit in the naturally formed concavity present in the bottom surface of a spinous process.

In one embodiment, the interspinous spacer preferably includes a W-shaped or S-shaped leaf spring for insertion between the adjacent superior and inferior spinous processes, the leaf spring having a top surface for contacting the superior spinous process and a bottom surface for contacting the inferior spinous process and engagement means extending from the leaf spring for securing the spacer to the adjacent spinous processes.

BRIEF DESCRIPTION OF THE DRAWINGS

The foregoing summary, as well as the following detailed description of the preferred embodiments of the application, will be better understood when read in conjunction with the appended drawings. For the purposes of illustrating the device of the present application, there is shown in the drawings preferred embodiments. It should be understood, however, that the application is not limited to the precise arrangements and instrumentalities shown. In the drawings.

DETAILED DESCRIPTION OF THE INVENTION

Certain terminology is used in the following description for convenience only and is not limiting. The words "right", "left", "top" and "bottom" designate directions in the drawings to which reference is made. The words "inwardly" and "outwardly" refer to directions toward and away from, respectively, the geometric center of the device and designated parts thereof. The words, "anterior", "posterior", "superior", "inferior" and related words and/or phrases designate preferred positions and orientations in the human body to which reference is made and are not meant to be limiting. The terminology includes the above-listed words, derivatives thereof and words of similar import.

Certain exemplary embodiments of the invention will now be described with reference to the drawings. In general, such embodiments relate to an interspinous spacer for implantation and/or affixation between spinous processes of adjacent superior and inferior vertebrae to treat spinal stenosis.

The interspinous spacer may be used to treat spinal stenosis in combination with decompression. Alternatively, the interspinous spacer may be used to treat spinal stenosis without any additional treatment. Especially in the situation where decompression is used, it is desirable to restore at least part of the stability of the spine with an interspinous spacer.

In use, the interspinous spacer of the present invention, may allow for application of a distractive force as well as a compressive force to the same spinal level (e.g. distractive force in case of extension of the spine and compressive force in case of flexion of the spine). The interspinous spacer preferably also enables patient to patient constant distractive and/or compressive forces by incorporating a defined contact area to the spinous process, as will be described in greater detail below, which facilitates reproducible conditions (e.g., transmittal forces) at the spacer to bone interface. The interspinous spacer also enables faster, simpler and safer (e.g., reduced bone damage) attachment to the adjacent spinous processes.

The interspinous spacer may be made from any biocompatible material including but not limited to metals such as, for example, titanium, titanium alloys, stainless steel, etc., polymers such as, for example, PEEK, PCU, etc., and combinations thereof. In the situation where the spacer is manufactured from PEEK, the combination of an elastic rubber like polymer may be used to allow for the required large deformations and high loads.

As generally understood by one of ordinary skill in the art, it should be understood that while the interspinous spacer will be described in connection with posterior spinal fixation, those skilled in the art will appreciate that the spacer as well as the components thereof may be used for fixation in other parts of the body.

Referring to FIGS. 1-4, the interspinous spacer 10 may include a body member 20 sized and configured for insertion between adjacent spinous processes SP. The interspinous spacer 10 may also include engagement means 40 for attaching the body member 20 to the adjacent spinous process SP.

Preferably, as shown, the body member 20 is in the form of a "W-shaped" leaf spring 21. The W-shaped leaf spring 21 preferably includes a top bone contacting surface 22 for contacting the superior spinous process SP, a bottom bone contacting surface 24 for contacting the inferior spinous process SP, and an elastically flexible central portion 26 for enabling compression and/or extension of the spacer 10.

Figure 14:
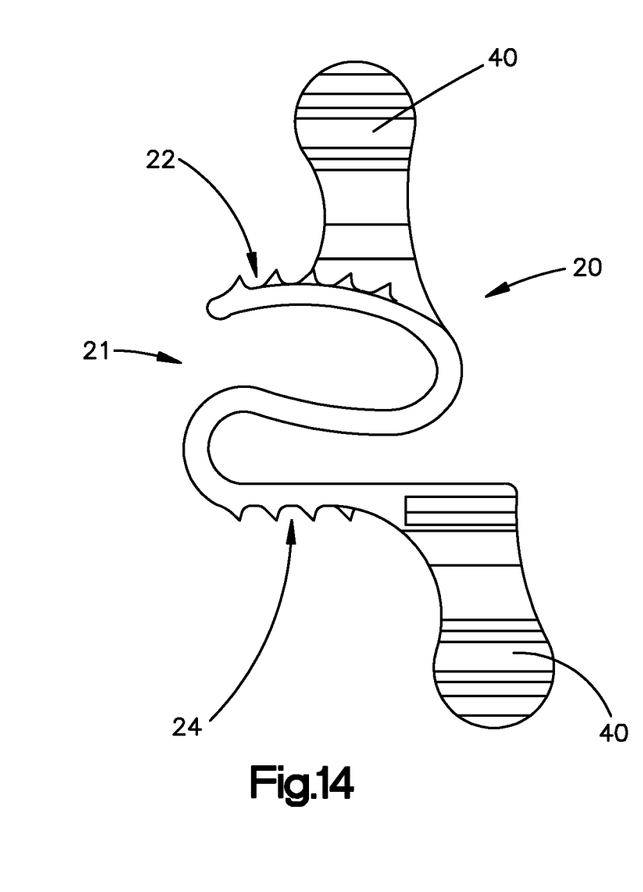
FIG. 14 illustrates a side view of an alternate exemplary embodiment of an interspinous spacer, the spacer including an S-shaped leaf spring.

Alternatively, as shown in FIG. 14, the body member 20 may be in the form of an "S-shaped" leaf spring 21. By providing an S-shaped leaf spring 21, the spacer is able to provide many of the same benefits as a spacer formed with a W-shaped leaf spring (as will be described below) but with a more compact design. It should be noted that while the remaining embodiments illustrate and discuss a W-shaped leaf spring, it is envisioned that the W-shaped leaf spring can be replaced by an S-shaped leaf spring.

By providing a W-shaped or S-shaped leaf spring, the interspinous spacers of the present invention are more forgiving regarding point of load transmission between the interspinous spacer and the adjacent spinous processes SP. That is, because of the W-shaped or S-shaped leaf spring, the stiffness of the spacer, depending on the point of contact, varies little compared to the huge variance in stiffness of, prior art interspinous spacers including, for example, a C-shaped spacer. That is, in a C-shaped spacer, for example, a force applied to the anterior portion of the top and bottom bone contacting surfaces will encounter a high stiffness spacer while a force applied to the posterior portion of the top and bottom bone contacting surfaces will encounter a low stiffness spacer. This is because the forces applied to a C-shaped leaf spring will encounter a single loop and therefore will depend greatly on each other and on the location of where the force is applied. In contrast, forces applied to the anterior and posterior portions of the W-shaped and S-shaped leaf spring will encounter different loops and therefore the stiffness can be adjusted at the anterior portion and at the posterior portion and although there will be a difference depending on the contact point, the stiffness will be more uniform than for a C-shaped spacer.

Figure 1:
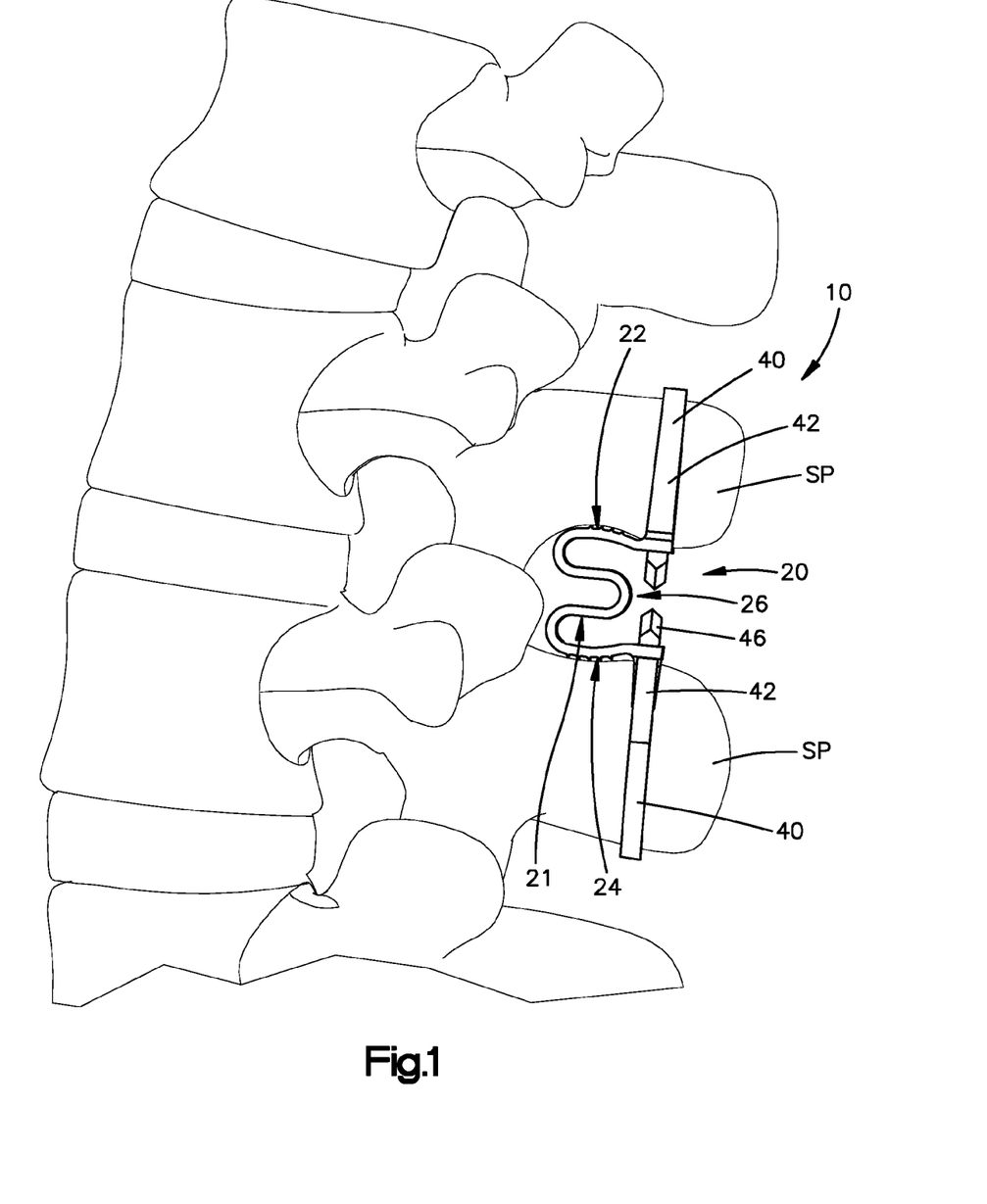
FIG. 1 illustrates a side view of an exemplary embodiment of an interspinous spacer, the spacer including a W-shaped leaf spring.
Figure 2:
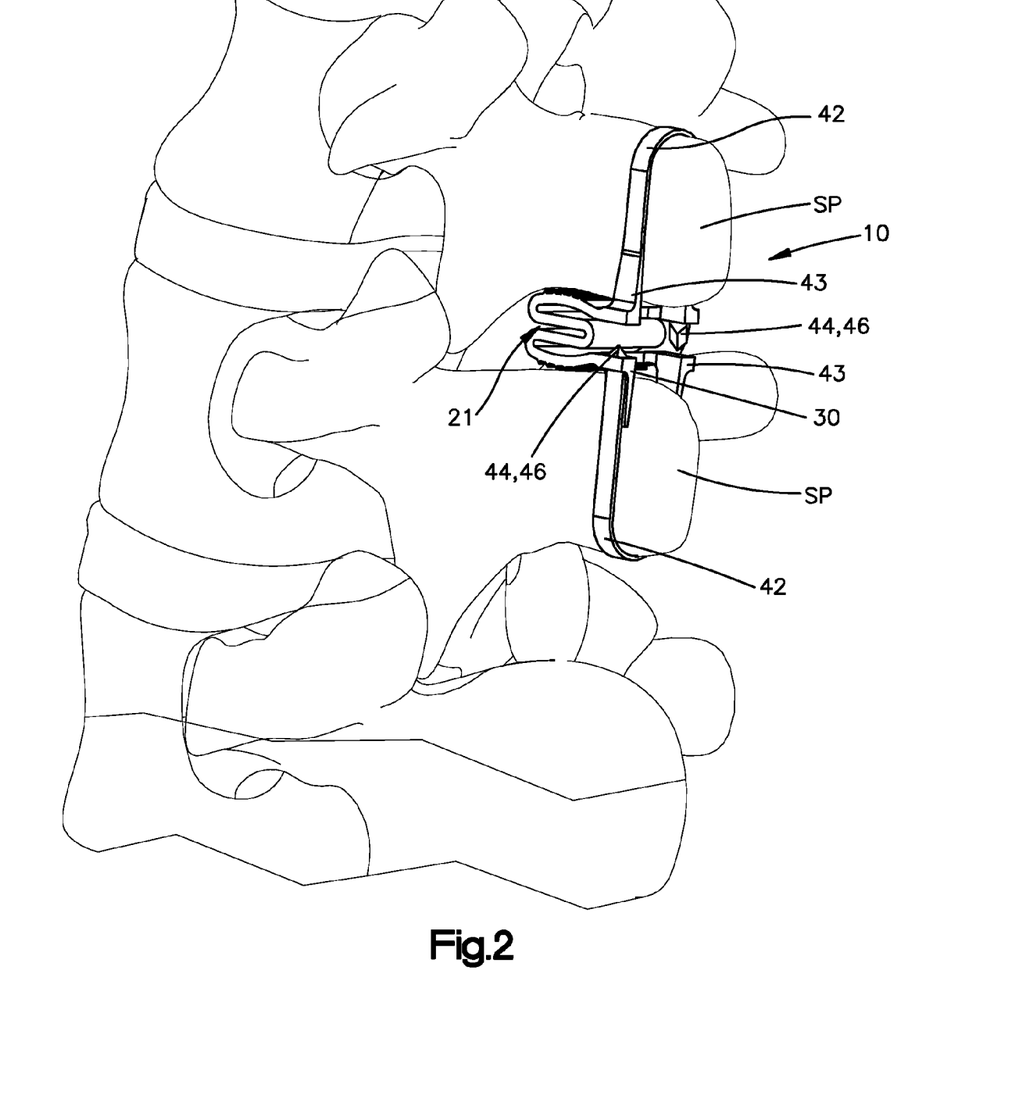
FIG. 2 illustrates a perspective view of the interspinous spacer shown in FIG. 1.
Figure 3:
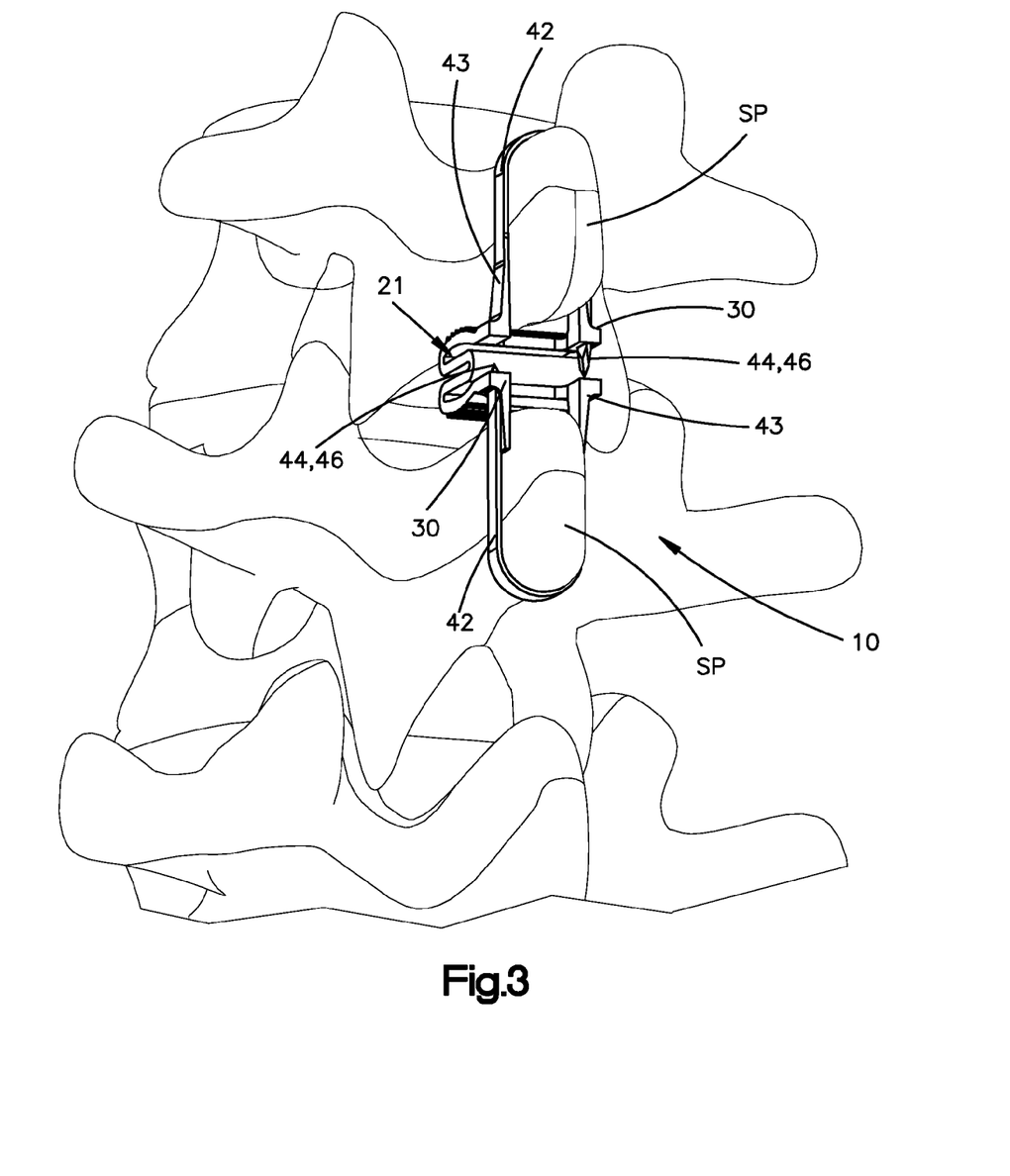
FIG. 3 illustrates another perspective view of the interspinous spacer shown in FIG. 1.

The engagement means 40 preferably is in the form of one or more wire straps 42 attached to the W-shaped leaf spring 21, more preferably the top and bottom surfaces 22, 24 of the W-shaped lead spring 21. The wire straps 42 include a first end 43, a second end 44 and a length. As best shown in FIGS. 2 and 3, the first end 43 of the strap 42 is preferably connected to, and may be integrally formed with, the W-shaped leaf spring 21. The W-shaped leaf spring 21 preferably also includes a locking mechanism 30. As shown, the locking mechanism 30 may include a component extending from the W-shaped leaf spring 21 or an opening formed in the W-shaped leaf spring 21 on the opposite side of the wire strap 42. In use, the wire strap 42 extends from the W-shaped leaf spring 21, along one side of one of the adjacent spinous process SP, over or under the adjacent spinous process SP to the other side, and back to the W-shaped leaf spring 21 wherein the wire strap 42 can be inserted into the locking component 30 to secure the spacer 10 to the adjacent spinous process SP.

Figure 4:
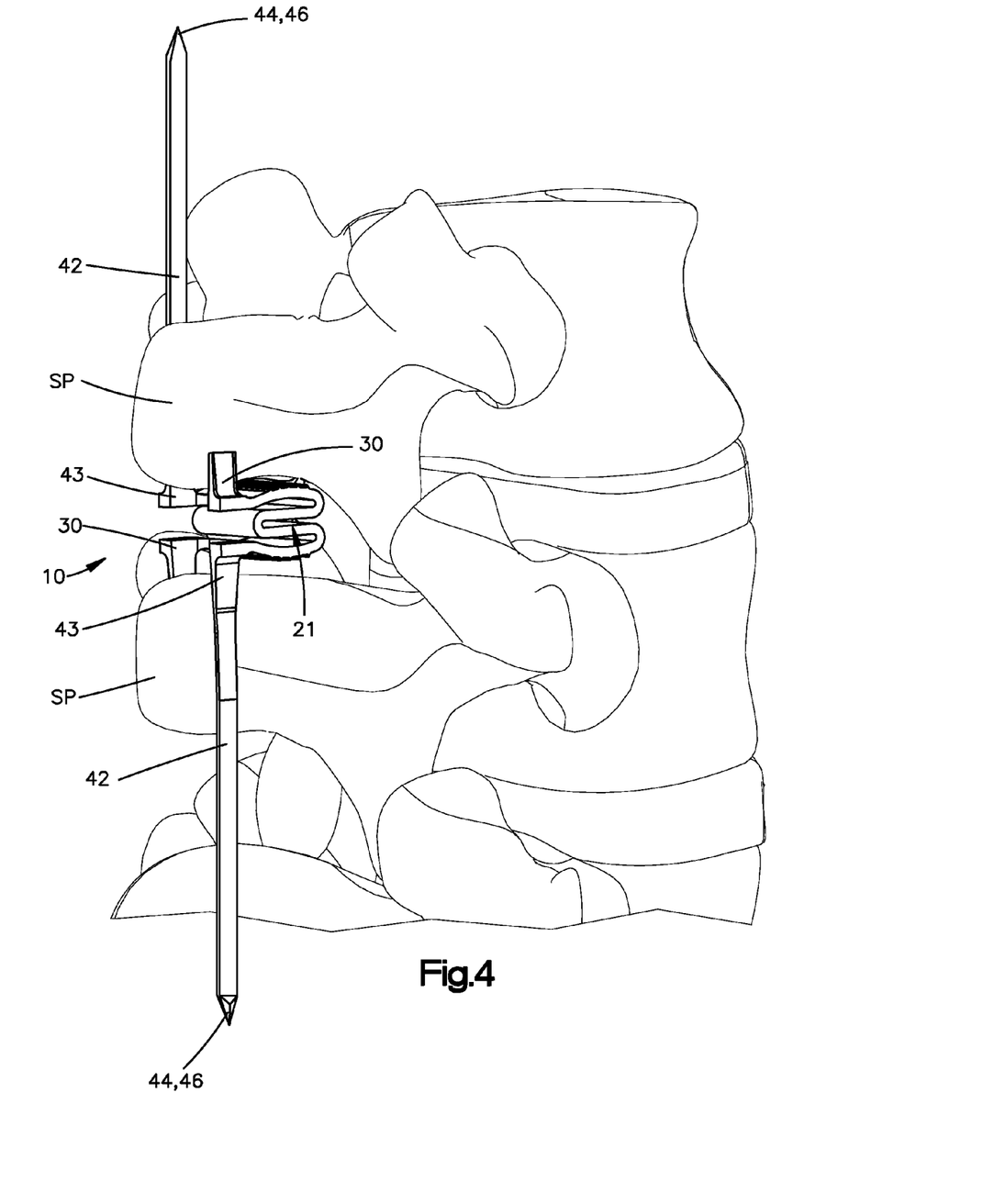
FIG. 4 illustrates another perspective view of the interspinous spacer shown in FIG. 1 with untied wire straps.

As best shown in FIG. 4, the second end 44 of the wire straps 42 preferably includes an integrated cutting blade 46 formed on a tip thereof. The integrated cutting blade 46 formed on the end of the wire strap 42 allows the wire strap 42 to cut through the interspinous ligament as the wire strap 42 is passed from one side of the spinous process SP to the other. Any excessive remaining length of the wire strap 42, after it has been secured to the spinous process SP may be cut off and removed.

In use, preferably, the W-shaped interspinous spacer 10 is inserted as ventral (e.g., anteriorly) as possible. The top and bottom bone contacting surfaces 22, 24 of the W-shaped leaf spring 21 (e.g. the portions of the leaf spring which contact the adjacent spinous process) preferably include a length in the anterior-posterior direction which is shorter than the length of the adjacent spinous processes in the anterior-posterior direction to permit distractive forces to be applied to the adjacent spinous processes in a defined area. Preferably the defined area is as far ventral as possible in order to reduce variations of spacer performance (e.g. stiffness) due to anatomical variations (e.g., shape of adjacent spinous process and therefore shape of contact area).

The wire straps 42 are preferably located and/or affixed to the adjacent spinous process SP posteriorly of the W-shaped leaf spring 21 to permit, in case of flexion, lower spacer stiffness with respect to extension. In use, having lower stiffness in flexion as compared to extension is desirable because the angle neutral flexion is generally larger than the angle neutral-extension and therefore it is preferable to hinder flexion less than extension.

Figure 5:
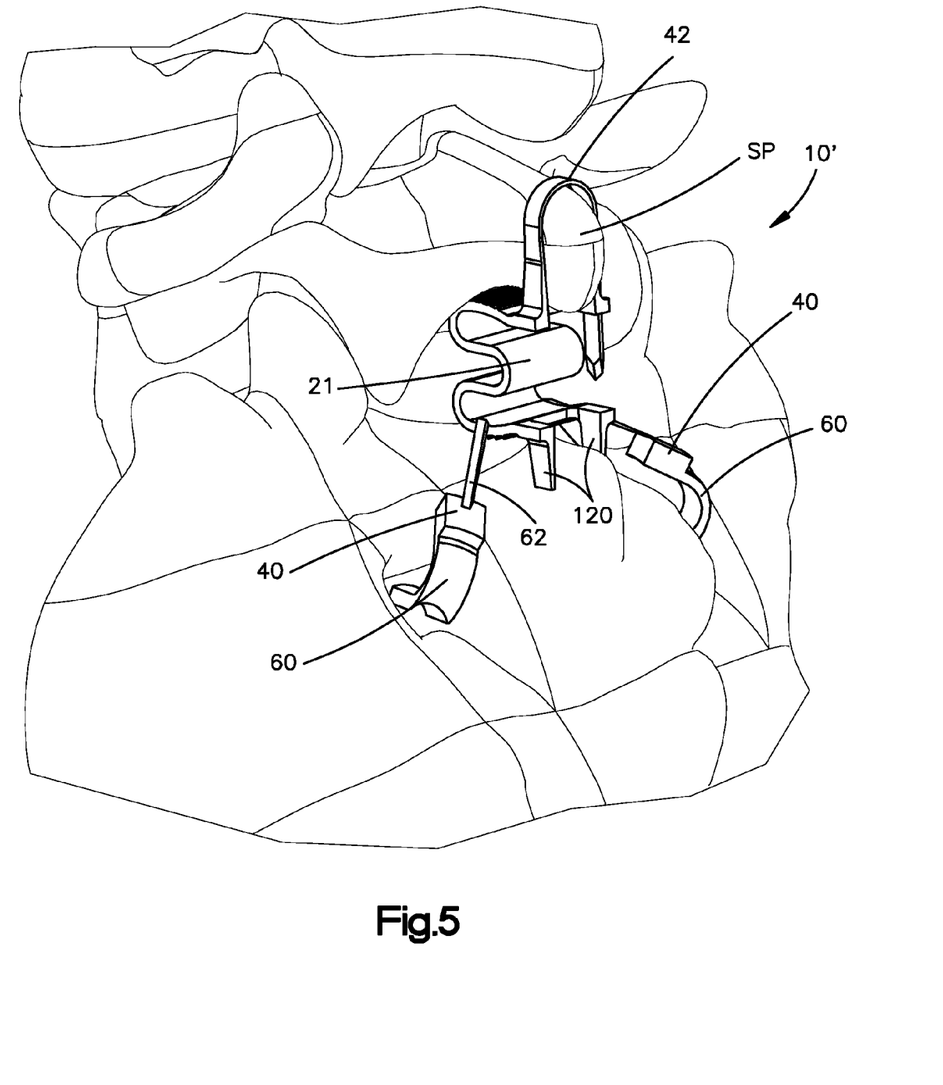
FIG. 5 illustrates a perspective view of another exemplary embodiment of an interspinous spacer, the spacer including a W-shaped leaf spring.
Figure 6:
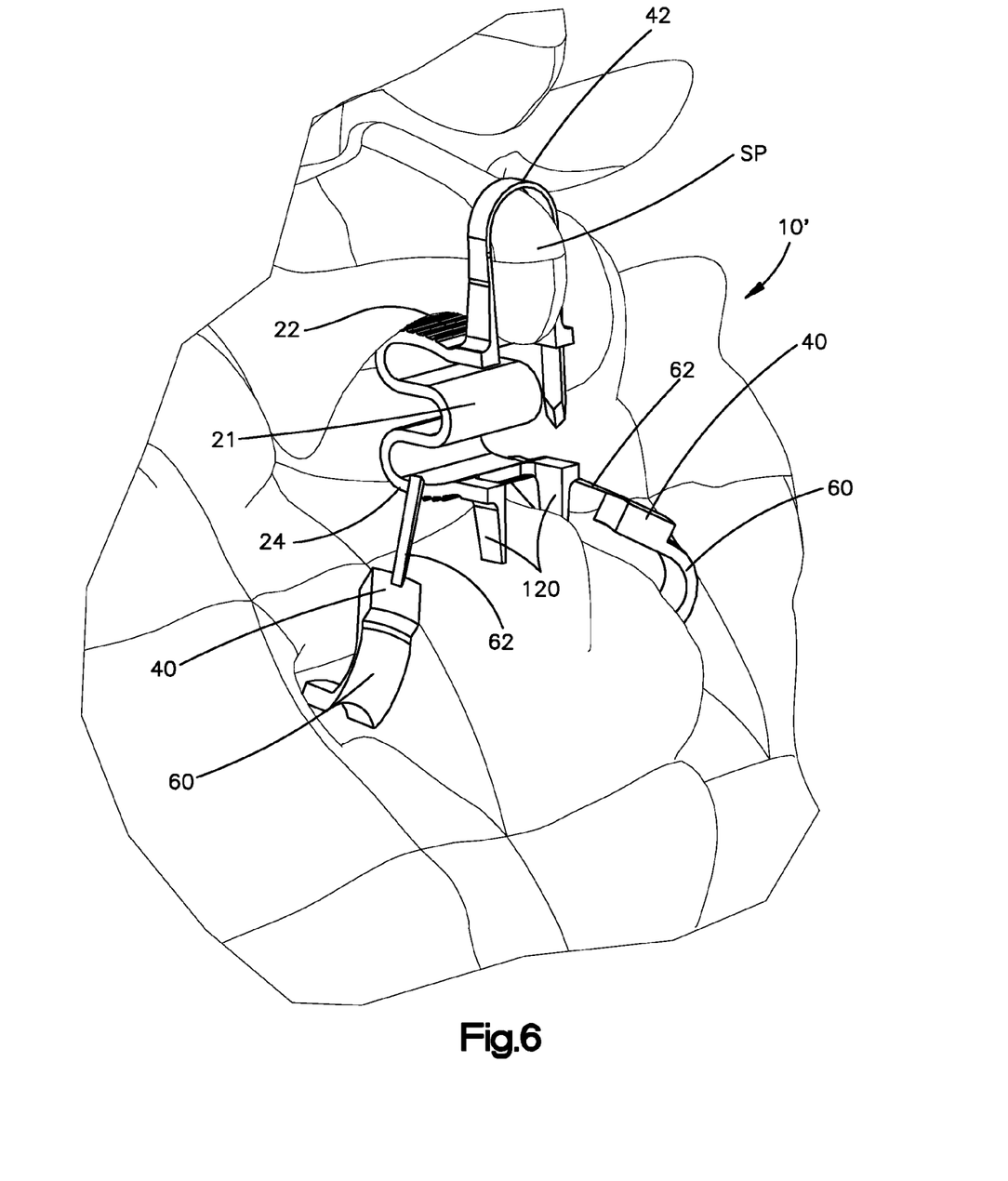
FIG. 6 illustrates another perspective view of the interspinous spacer shown in FIG. 5.
Figure 7:
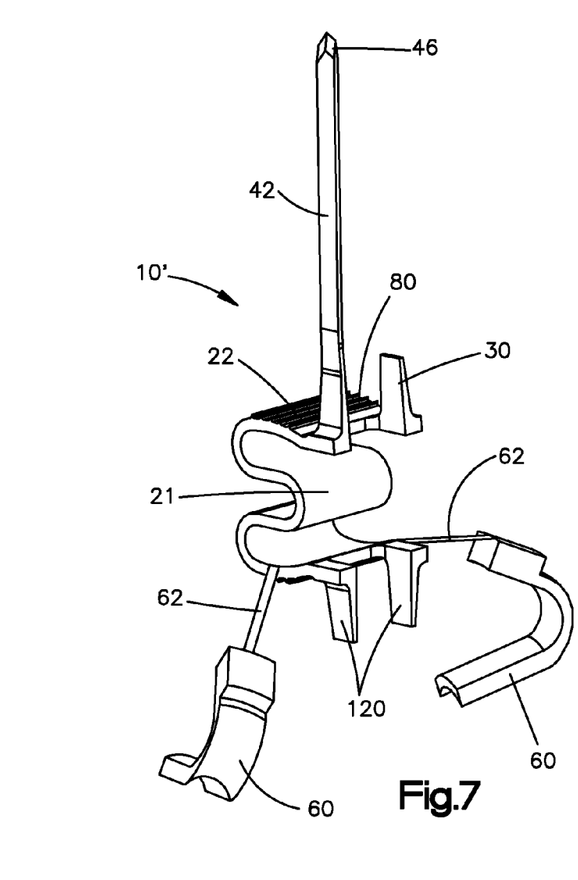
FIG. 7 illustrates another perspective view of the interspinous spacer shown in FIG. 5 with untied wire straps.

As best shown in FIGS. 5-7, rather than incorporating a pair of wire straps 42 (as shown in FIGS. 1-4), the engagement means 40 may be in the form of one or more pair of hooks 60 for engaging an adjacent spinous process SP. As shown, the spacer 10' may include a wire strap 42 for engaging the superior spinous process SP and a pair of hooks 60 for engaging the inferior spinous process SP. Incorporation of one or more hooks 60 instead of a wire strap 42 is particularly useful for implantation at the L5/S1 level of the lumbar spine since the spinous process at the S1 level does not generally permit attaching a wire strap 42. Thus, as shown, preferably the interspinous spacer 10' may include a wire strap 42 extending from the top bone contacting surface 22 of the W-shaped leaf spring 21 for engaging the L5 spinous process and a pair of hooks 60 extending from the bottom bone contacting surface 24 of the W-shaped leaf spring 21 for attaching to the S1. Alternatively, the interspinous spacer 10' may include a wire strap 42 extending from the bottom bone contacting surface 24 and a pair of hooks 60 extending from the top bone contacting surface 22, or a pair of hook members 60 extending from both the top and bottom bone contacting surfaces 22, 24 of the W-shaped leaf spring 21. Preferably the hooks 60 are sized and configured to engage the foramina of the sacrum.

The hooks 60 may also include a wire or cable 62 for connecting the hooks 60 to the W-shaped leaf spring 21. Preferably, the wire or cable 62 interconnects the hook 60 and the W-shaped leaf spring 21 in a manner that allows for a surgeon to adjust the relative length between the hook 60 and the W-shaped leaf spring 21. It should be noted that other forms are connecting the hook 60 to the W-shaped leaf spring 21 may also be used. The bottom surface 24 of the W-shaped leaf spring 21 may include a pair of guides 120, as will be described in greater detail below, for assisting the surgeon to properly position the spacer 10'.

It should be further noted that although the interspinous spacer 10' disclosed in FIGS. 5-7 has been described for use in connection with the L5/S1 level of fixation, the interspinous spacer 10' can be used to connect adjacent spinous process SP anywhere along the spine.

Figure 8:
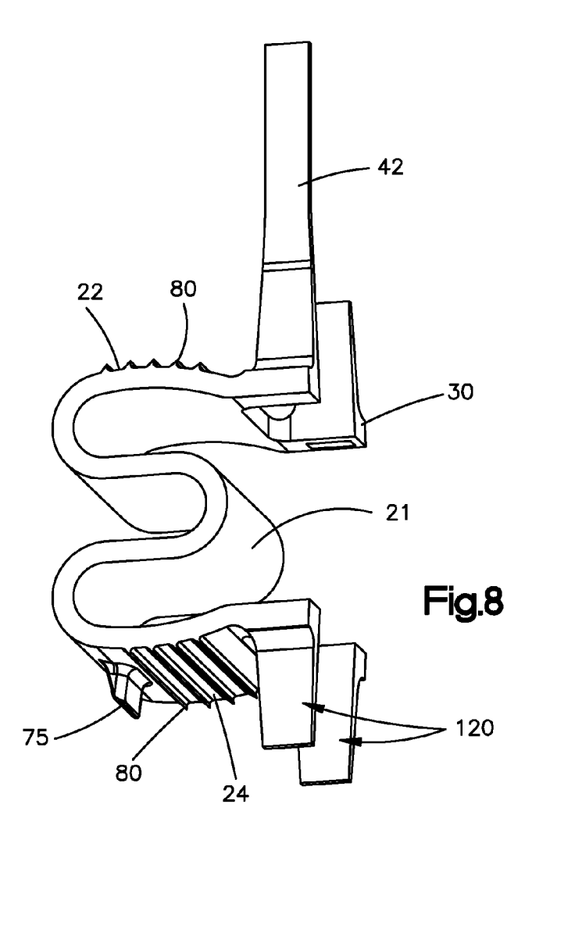
FIG. 8 illustrates a side view of another exemplary embodiment of an interspinous spacer, the spacer including a W-shaped leaf spring.

As best shown in FIG. 8, the W-shaped leaf spring 21 may also include a lamina hook 75 for contacting and/or engaging one of the adjacent spinous process SP. Preferably, the lamina hook 75 is formed on and/or extends from the bottom bone contacting surface 24 of the W-shaped leaf spring 21. Although the lamina hook 75 could also be formed on and/or extend from the top bone contacting surface 22 of the W-shaped leaf spring 21. The lamina hook 75 is sized and configured to engage the spinous process SP to prevent the interspinous spacer 10, 10' from slipping and/or moving posteriorly thus allowing, for example, the interspinous spacer 10, 10' to be inserted in a situation were the S1 spinous process may not be sufficiently developed, in such a situation the interspinous spacer 10, 10' may rest on the edge of the S1 lamina without risk of migration.

As best shown in FIGS. 7 and 8, the top and bottom bone contacting surfaces 22, 24 of the W-shaped leaf spring 21 may also include one or more projections 80, such as, for example, teeth, ridges, etc. for contacting the adjacent surfaces of the spinous process SP.

It should be noted that although the lamina hook 75 and projections 80 have been shown and described in connection with the interspinous spacers 10' disclosed in FIGS. 5-8, these features may also be used in connection with the interspinous spacer 10 disclosed in FIGS. 1-4, and any other interspinous spacer.

Referring to FIGS. 9A-9D, the spacer 10" may include a W-shaped leaf spring 21 may include a top bone contacting surface 22 having a convex shape to contact the lower surface of the superior spinous process SP while the bottom bone contacting surface 24 may be substantially flat or straight for contacting the upper surface of the inferior spinous process SP. By providing a convex shaped top bone contacting surface 22, the interspinous spacer 10, 10', 10" is better able to sit in the ideal anterior/posterior position, namely, in the naturally formed concavity present in a bottom surface of a spinous process. The W-shaped leaf spring 21 preferably also includes a tapered side surface 28 (e.g., narrowing the width of the surface connecting the top bone contacting surface 22, the elastically flexible central portion 26 and the bottom bone contacting surface 24). By providing a tapered lateral surface 28, the interspinous spacer 10, 10', 10" is better able to be positioned in the ideal anterior/posterior position without contacting either the facet joints or laminae.

As further illustrated in FIGS. 9A-9D, the engagement means 40 formed on the interspinous spacer 10" may be in the form of a plurality of wings 100 extending from the top and bottom bone contacting surfaces 22, 24 for contacting the sides of the adjacent spinous processes SP. Preferably, the wings 100 are pre-bent so that the wings 100 diverge as they move away from the top and bottom bone contacting surfaces 22, 24. By pre-bending the wings 100, the spacer 10" is better able to receive the superior and inferior spinous processes SP without the necessity of spreading the wings 100 open first. Thus, pre-bending the wings 100 simplifies the implantation process. Thereafter, once the interspinous spacer 10" has been properly positioned between the adjacent spinous processes SP, the wings 100 can be crimped against the adjacent spinous process SP by the surgeon to thereby secure the position of the spacer 10" with respect to the adjacent vertebrae. As show, the interior surface of the wings 100 preferably includes a plurality of teeth or ridges 102 for engaging the sides of the adjacent spinous processes SP to better secure the spacer 10" relative to the vertebrae.

The wings 100 are also preferably staggered such that the superior wings 100a are positioned more anteriorly as compared to the inferior wings 100b. By providing staggered wings 100a, 100b, the superior wings 100a can serve as a mechanical stop regarding implantation depth by making contact with the superior laminae.

It should be noted that although the convex shaped top bone contacting surface 22 and/or the staggered wings 100 have been shown and described in connection with the interspinous spacers 10" disclosed in FIGS. 9A-9D, these features may also be used in connection with the interspinous spacer 10, 10' disclosed in FIGS. 1-7, and any other interspinous spacer.

Figure 9A:
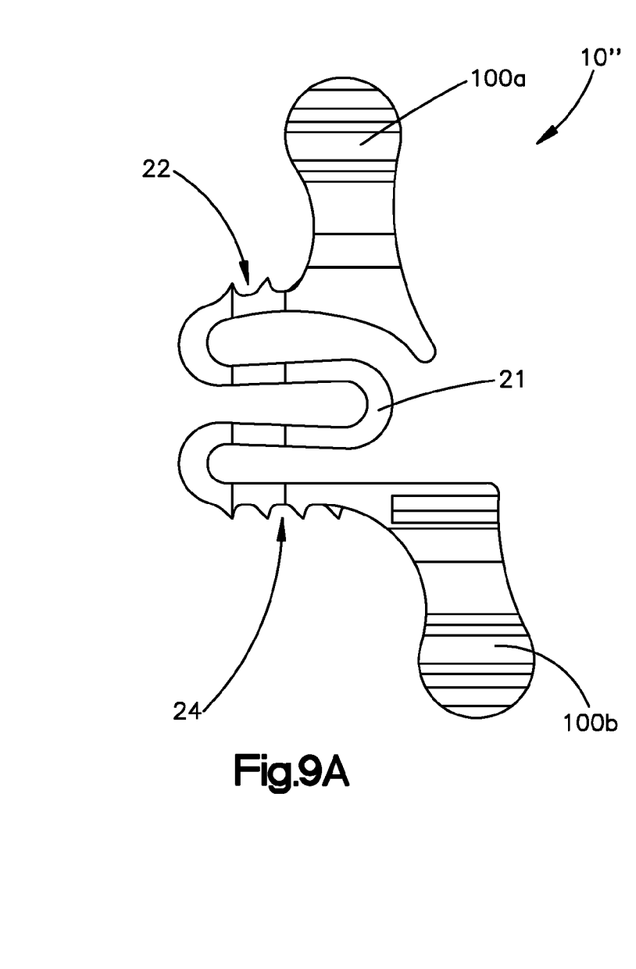
FIG. 9A illustrates a side view of another exemplary embodiment of an interspinous spacer, the spacer including a W-shaped leaf spring.
Figure 9B:
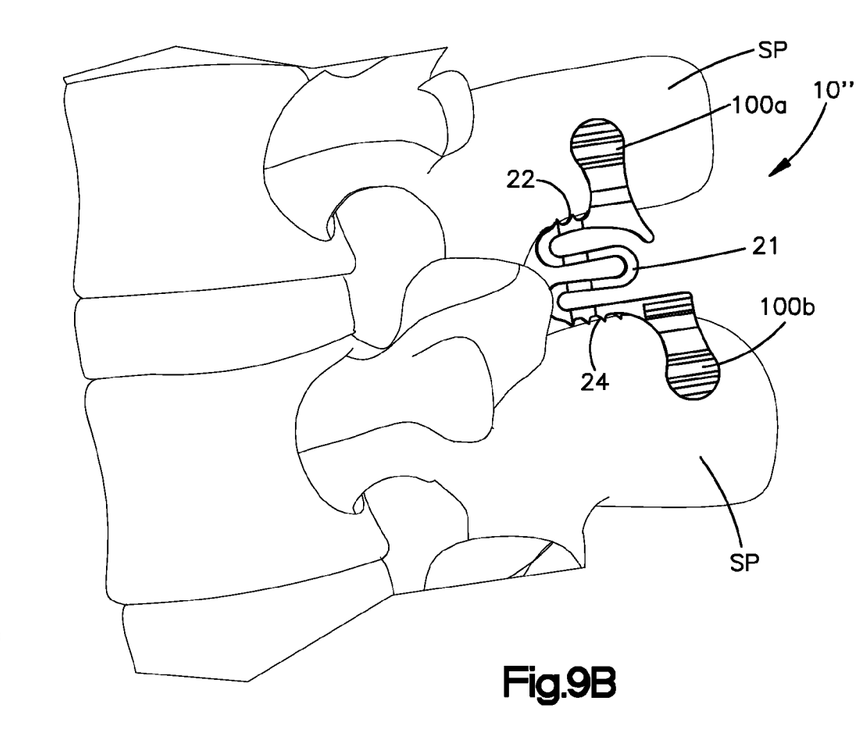
FIG. 9B illustrates another side view of the interspinous spacer shown in FIG. 9A.
Figures 9C, 9D, 9E:
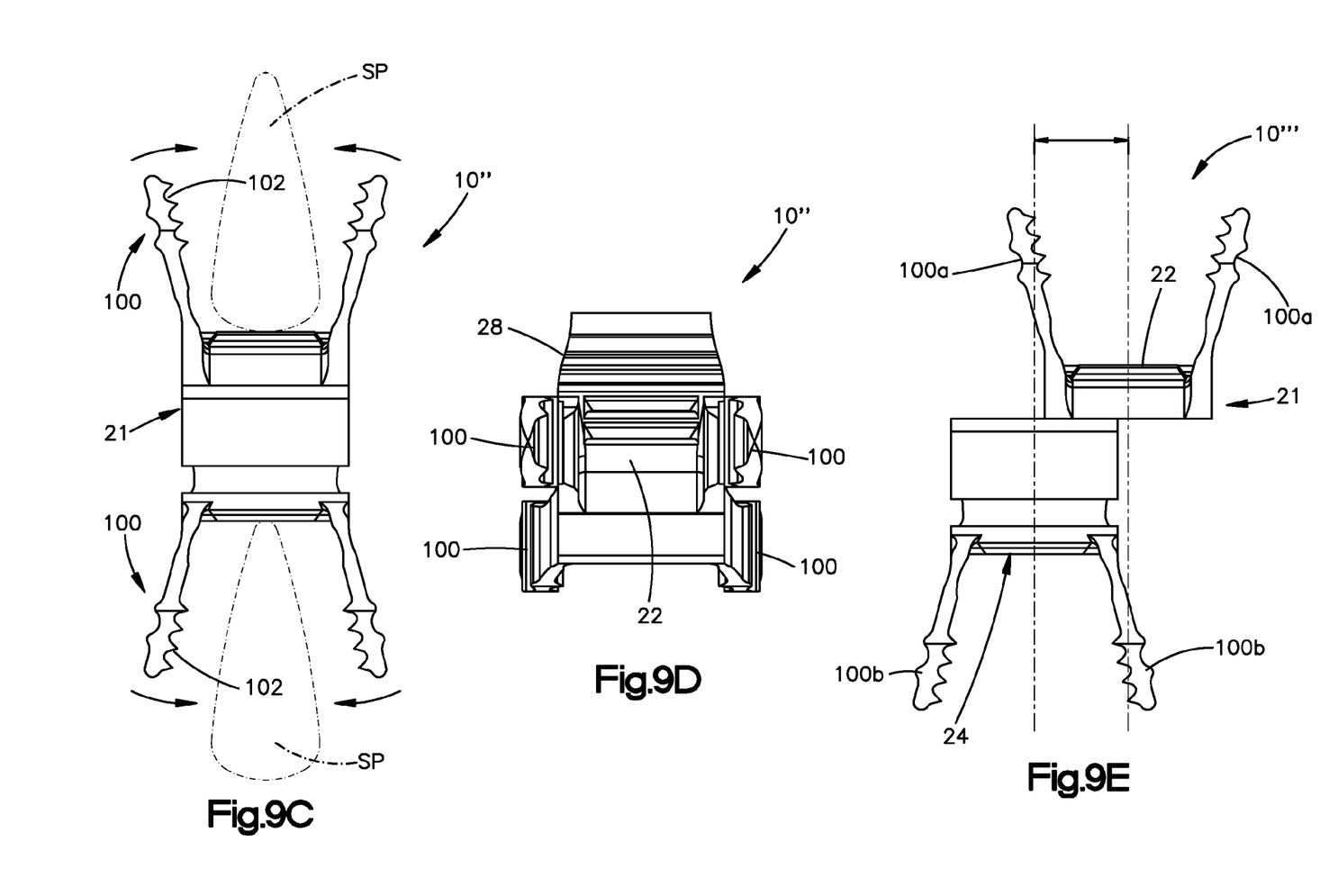
FIG. 9C illustrates a rear view of the interspinous spacer shown in FIG. 9A.
FIG. 9D illustrates a top view of the interspinous spacer shown in FIG. 9A.
FIG. 9E illustrates a rear view of another exemplary embodiment of an interspinous spacer, the spacer including a W-shaped leaf spring.

Referring to FIG. 9E, the spacer 10''' may alternatively include superior and inferior wings 100a, 100b wherein the superior wings 100a are laterally offset from the inferior wings 100b. By providing lateral offset superior and inferior wings 100a, 100b, the interspinous spacer 10''' is better able to accommodate spinous processes SP that are not aligned due to, for example, degenerative scoliosis.

Figure 10A:
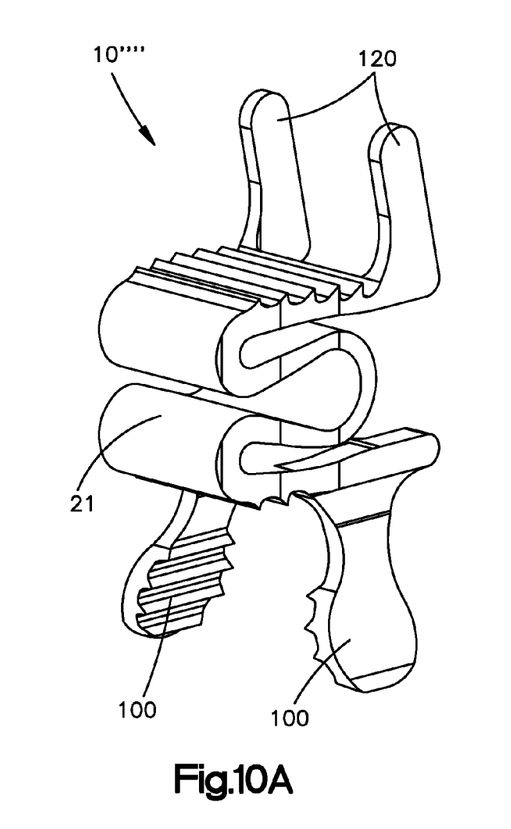
FIG. 10A illustrates a perspective view of another exemplary embodiment of an interspinous spacer, the spacer including a W-shaped leaf spring.
Figure 10B:
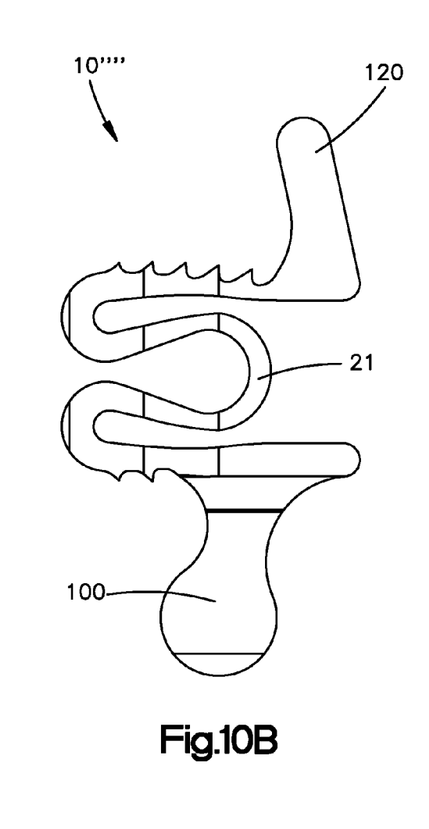
FIG. 10B illustrates a side view of the interspinous spacer shown in FIG. 10A.
Figure 10C:
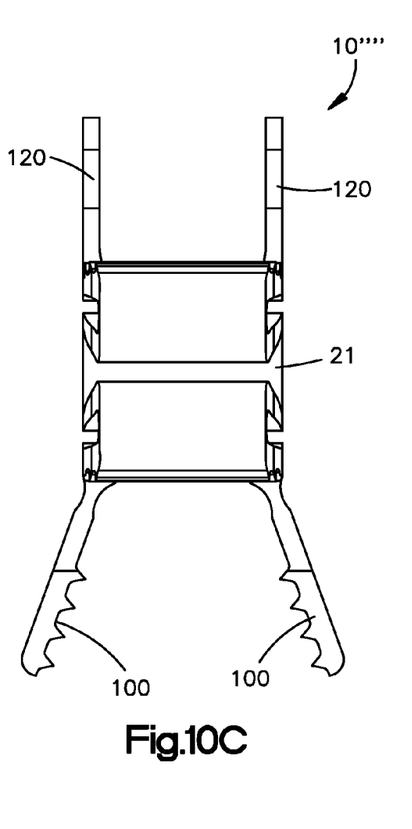
FIG. 10C illustrates a rear view of the interspinous spacer shown in FIG. 10A.

Referring to FIGS. 10A-10C, the interspinous spacer 10'''' may include a pair of guide members 120 in place of the superior wings 100a. In use, the guide members 120 are not crimped to the spinous process SP but serve only as a guide during and after implantation of the spacer 10''''. Alternatively, the pair of guide members 120 may be used in place of the inferior wings 100b.

Figures 11A, 11B:
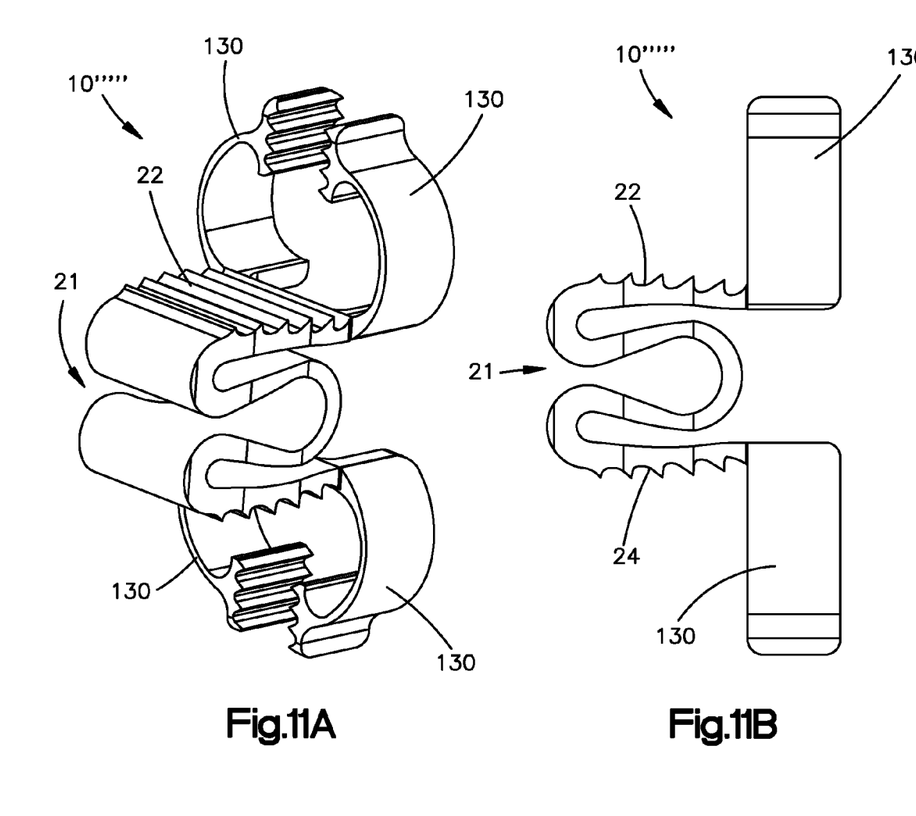
FIG. 11A illustrates a perspective view of another exemplary embodiment of an interspinous spacer, the spacer including a W-shaped leaf spring.
FIG. 11B illustrates a side view of the interspinous spacer shown in FIG. 11A.
Figure 11C:
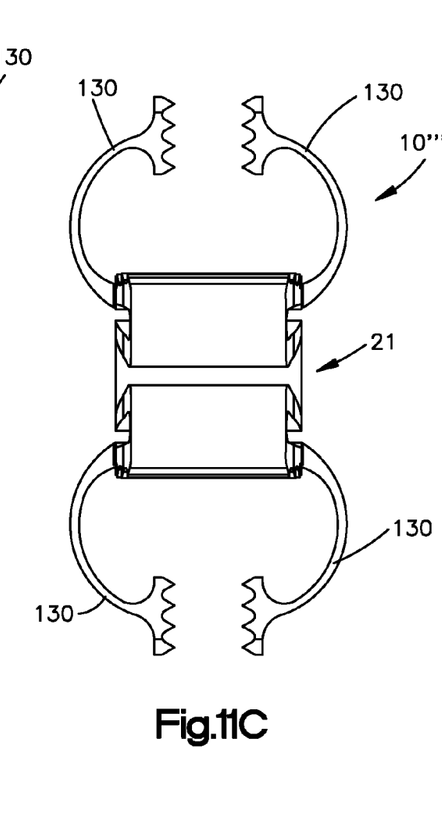
FIG. 11C illustrates a rear view of the interspinous spacer shown in FIG. 11A.

Referring to FIGS. 11A-11C, the superior and inferior wings 100a, 100b may be replaced by elastic projections 130 for attaching the spacer 10'''' to the adjacent spinous processes SP. In use, the elastic projections 130 are biased closed so that the projections 130 automatically engage the spinous process SP without the need to actively crimp the projections 130 against the spinous process SP as is generally required by the wings 100. In use, the elastic projections 130 may be held open during implantation of the spacer 10''''. Once the spacer 10'''' has been properly positioned, the elastic projections 130 may automatically compress against the side surface of the spinous process SP upon removal of the insertion instrument.

Figures 12A, 12B:
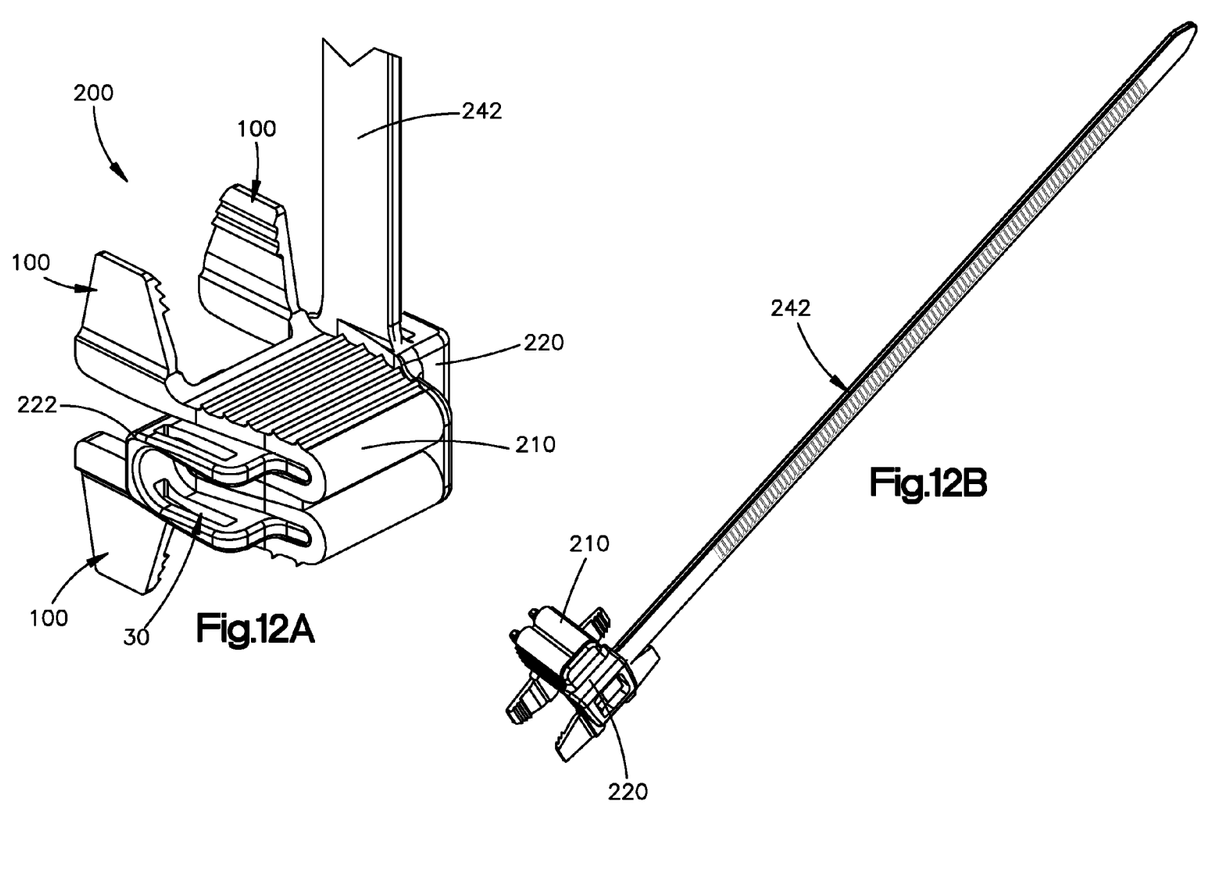
FIG. 12A illustrates a perspective view of another exemplary embodiment of an interspinous spacer, the spacer including a W-shaped leaf spring.
FIG. 12B illustrates another perspective view of the interspinous spacer shown in FIG. 12A with the wire strap fully extended.

Referring to FIGS. 12A and 12B, the interspinous spacer 200 may be formed from two or more components. As shown, the interspinous spacer 200 may be formed from a first component 210 coupled to a second component 220 wherein the first component 210 may be in the form of a W-shaped interspinous spacer 21, as described above, while the second component 220 may be in the form of an insert 222 having a wire-strap 242. In use, incorporation of the insert 222 provides for a stiffer interspinous spacer 200.

Figure 13:
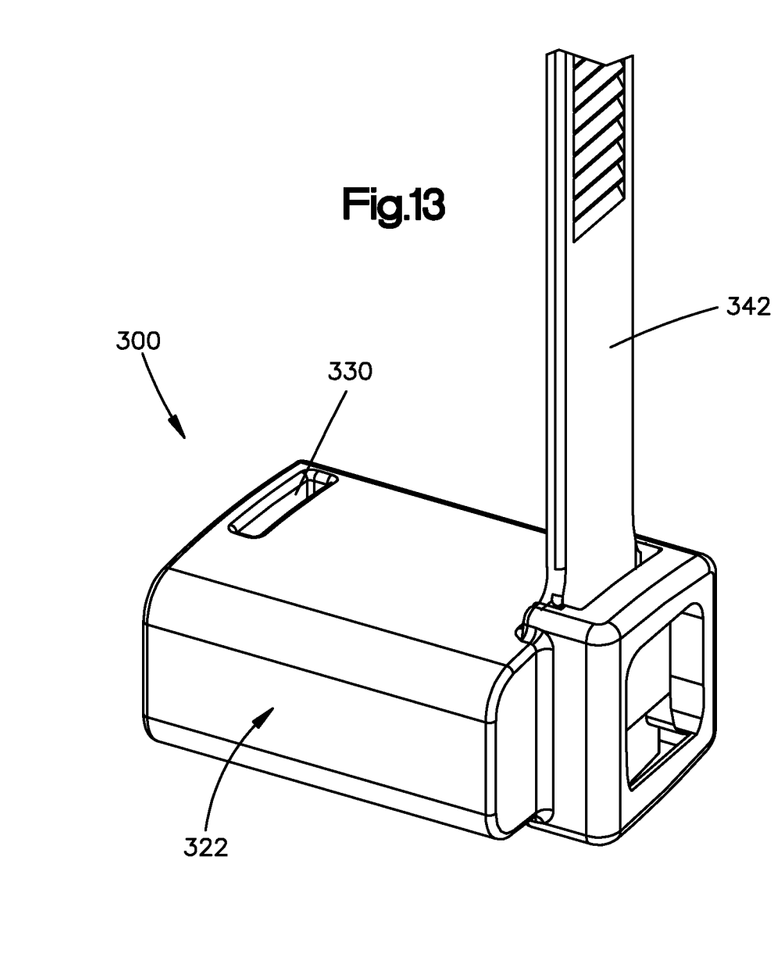
FIG. 13 illustrates a perspective view of another exemplary embodiment of an interspinous spacer.

Referring to FIG. 13, the insert 322 may be configured as a stand-alone spacer 300 for implantation between adjacent spinous processes SP. As show, the spacer 300 may include an integrated wire strap 342 and locking component 330 for securing the spacer 300 between the adjacent spinous process SP.

The top and bottom bone contacting surfaces 22, 24 of the W-shaped leaf spring 21 may include a layer of "soft" material (e.g., material having a lower modulus of elasticity) or foam to facilitate better load distribution at the spacer/bone interface. The foam may be in the form of, for example, titanium foam, PEEK foam, etc. In the case of a soft material, the layer may deform in areas of high pressure resulting in an increase in contact area and a corresponding reduction in pressure. In cases where a foam is used, the foam layer may collapse in areas of high contact pressure resulting in an increase in contact area and a corresponding reduction in pressure.

It should be noted that although certain features have been illustrated and described in connection with certain embodiments, these features are interchangeable and may be used with any interspinous spacer described herein.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. An interspinous spacer for implantation between adjacent superior and inferior spinous processes defining a sagittal plane extending therethrough, the spacer comprising:
    one of a W-shaped leaf spring and a S-shaped leaf spring for insertion between the adjacent superior and inferior spinous processes, the leaf spring having a top surface for contacting the superior spinous process and a bottom surface for contacting the inferior spinous process, the leaf spring including at least one loop; and
    at least one engagement member extending from the leaf spring for securing the spacer between the adjacent spinous processes in a position wherein the loop undulates in the sagittal plane extending through the adjacent spinous processes; wherein at least one of the top and bottom surfaces includes a plurality of teeth for engaging the adjacent spinous process.

2. The spacer of claim 1, wherein the engagement member includes one or more wire straps, each wire strap including a first end operatively associated with the leaf spring, a second end, and a length, the wire strap being sized and configured to extend from one side of the leaf spring, over or under one of the spinous process to the other side of the spinous process.

3. The spacer of claim 2, wherein each wire strap is integrally formed with the leaf spring.

4. The spacer of claim 2, wherein the leaf spring includes an opening for receiving the second end of the wire strap.

5. The spacer of claim 2, wherein the second end of the wire strap includes a cutting blade.

6. The spacer of claim 1, wherein the top and bottom surfaces of the leaf spring have a length in an anterior-posterior direction which is shorter than a length of the adjacent spinous processes in the anterior-posterior direction.

7. The spacer of claim 1, wherein the spacer includes a pair of guide members extending from at least one of the top and bottom surfaces for guiding the spacer both during and after implantation.

8. The spacer of claim 1, wherein the engagement member includes one or more elastic projections extending from at least one of the top and bottom surfaces for engaging the superior and inferior spinous process, the elastic projections being sized and configured to automatically engage the superior and inferior spinous process.

9. The spacer of claim 1, wherein the leaf spring includes at least two loops and wherein the two loops complete full undulations within the plane when in the position.

10. The spacer of claim 9, wherein the loops are open loops configured to open in one of an anterior direction or a posterior direction within the plane when in the position.

11. An interspinous spacer for implantation between adjacent superior and inferior spinous processes defining a sagittal plane extending therethrough, the spacer comprising:
    one of a W-shaped leaf spring and a S-shaped leaf spring for insertion between the adjacent superior and inferior spinous processes, the leaf spring having a top surface for contacting the superior spinous process and a bottom surface for contacting the inferior spinous process, the leaf spring including at least one loop; and
    at least one engagement member extending from the leaf spring for securing the spacer between the adjacent spinous processes in a position wherein the loop undulates in the sagittal plane extending through the adjacent spinous processes; wherein the top surface is convex and the bottom surface is substantially flat.

12. The spacer of claim 11, wherein the top and bottom surfaces of the leaf spring have a length in an anterior-posterior direction which is shorter than a length of the adjacent spinous processes in the anterior-posterior direction.

13. The spacer of claim 11, wherein the spacer includes a pair of guide members extending from at least one of the top and bottom surfaces for guiding the spacer both during and after implantation.

14. The spacer of claim 11, wherein the engagement member includes one or more elastic projections extending from at least one of the top and bottom surfaces for engaging the superior and inferior spinous process, the elastic projections being sized and configured to automatically engage the superior and inferior spinous process.

15. The spacer of claim 11, wherein the leaf spring includes at least two loops and wherein the two loops complete full undulations within the plane when in the position.

16. The spacer of claim 15, wherein the loops are open loops configured to open in one of an anterior direction or a posterior direction within the plane when in the position.

17. An interspinous spacer for implantation between adjacent superior and inferior spinous processes defining a sagittal plane extending therethrough, the spacer comprising:
one of a W-shaped leaf spring and a S-shaped leaf spring for insertion between the adjacent superior and inferior spinous processes, the leaf spring having a top surface for contacting the superior spinous process and a bottom surface for contacting the inferior spinous process, the leaf spring including at least one loop; and
at least one engagement member extending from the leaf spring for securing the spacer between the adjacent spinous processes in a position wherein the loop undulates in the sagittal plane extending through the adjacent spinous processes; wherein the engagement member includes one or more pairs of wings extending from at least one of the top and bottom surfaces for engaging the superior and inferior spinous process; and further wherein wings include a pair of superior wings extending from the top surface and a pair of inferior wings extending from the bottom surface, the superior wings being staggered with respect to the inferior wings such that the superior wings are positioned more anteriorly as compared to the inferior wing.

18. The spacer of claim 17, wherein the top and bottom surfaces of the leaf spring have a length in an anterior-posterior direction which is shorter than a length of the adjacent spinous processes in the anterior-posterior direction.

19. The spacer of claim 17, wherein the superior wings are laterally offset with respect to the inferior wings.

20. The spacer of claim 17, wherein the spacer includes a pair of guide members extending from at least one of the top and bottom surfaces for guiding the spacer both during and after implantation.

21. The spacer of claim 17, wherein the leaf spring includes at least two loops and wherein the two loops complete full undulations within the plane when in the position.

22. The spacer of claim 21, wherein the loops are open loops configured to open in one of an anterior direction or a posterior direction within the plane when in the position.

23. An interspinous spacer for implantation between adjacent superior and inferior spinous processes defining a sagittal plane extending therethrough, the spacer comprising:
one of a W-shaped leaf spring and a S-shaped leaf spring for insertion between the adjacent superior and inferior spinous processes, the leaf spring having a top surface for contacting the superior spinous process and a bottom surface for contacting the inferior spinous process, the leaf spring including at least one loop; and
at least one engagement member extending from the leaf spring for securing the spacer between the adjacent spinous processes in a position wherein the loop undulates in the sagittal plane extending through the adjacent spinous processes; wherein the plane is a mid-sagittal plane and the loop undulates in the mid-sagittal plane.

24. The spacer of claim 23, wherein the top and bottom surfaces of the leaf spring have a length in an anterior-posterior direction which is shorter than a length of the adjacent spinous processes in the anterior-posterior direction.

25. The spacer of claim 23, wherein the spacer includes a pair of guide members extending from at least one of the top and bottom surfaces for guiding the spacer both during and after implantation.

26. The spacer of claim 23, wherein the engagement member includes one or more elastic projections extending from at least one of the top and bottom surfaces for engaging the superior and inferior spinous process, the elastic projections being sized and configured to automatically engage the superior and inferior spinous process.

27. The spacer of claim 23, wherein the leaf spring includes at least two loops and wherein the two loops complete full undulations within the plane when in the position.

28. The spacer of claim 27, wherein the loops are open loops configured to open in one of an anterior direction or a posterior direction within the plane when in the position.

* * * * *